United States Patent [19]

Arata et al.

[11] Patent Number: 4,822,909

[45] Date of Patent: Apr. 18, 1989

[54] 7-FLUOROPROSTAGLANDINS AND PROCESS FOR THEIR PRODUCTION

[75] Inventors: Yasuda Arata; Kato Masao, both of Yokohama; Yamabe Masaaki, Machida; Uchida Keiichi, Kawasaki, all of Japan

[73] Assignee: Asashi Glass Company Ltd., Tokyo, Japan

[21] Appl. No.: 60,088

[22] Filed: Jun. 9, 1987

Related U.S. Application Data

[62] Division of Ser. No. 06/702,790, Feb. 11, 1985, Pat. No. 4,699,989.

[30] Foreign Application Priority Data

Jun. 10, 1983 [JP] Japan ................. 58-102885

[51] Int. Cl.[4] .................................. C07C 177/00
[52] U.S. Cl. ......................... 560/121; 556/441; 549/415; 549/422; 549/473; 549/475; 560/106; 560/107; 560/118; 560/121; 560/231; 562/500; 562/503
[58] Field of Search ............... 560/121, 118, 231, 106, 560/107; 556/441; 562/500, 503; 549/415, 422, 473, 475

[56] References Cited

U.S. PATENT DOCUMENTS

4,454,339  6/1984  Skuballa .................. 560/55

OTHER PUBLICATIONS

Fieser et al, Reagents F Org. Syn. vol. 6 pp. 183–184 (1977) vol. 8 pp. 66–67 (1980).
Suzuki et al, Tet Letters 24 1187 (1983).
Riediker, J.A.C.S. 104 5842 (1982).

Primary Examiner—Robert Gerstl
Attorney, Agent, or Firm—Oblon, Fisher, Spivak, McClelland & Maier

[57] ABSTRACT

7-Fluoroprostaglandins represented by the following formula (I):

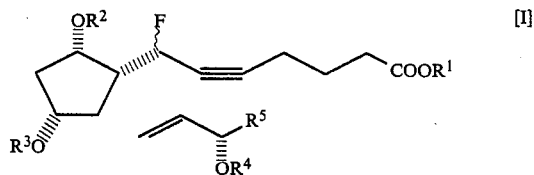

In the formula (I), $R^1$ is a hydrogen atom or an alkyl group having from 1 to 10 carbon atoms, $R^2$, $R^3$ and $R^4$ are hydrogen atoms or the same or different protective groups, respectively, and $R^5$ is a straight chained, branched or cyclic alkyl group having from 3 to 7 carbon atoms.

14 Claims, No Drawings

7-FLUOROPROSTAGLANDINS AND PROCESS FOR THEIR PRODUCTION

This is a division of application Ser. No. 06/702,790, filed Feb. 11, 1985, now U.S. Pat. No. 4,699,989.

FIELD OF TECHNOLOGY

The present invention relates to novel 7-fluoroprostaglandins and a process for their production.

Further, the present invention relates to a novel process for producing basically known 7-fluoroprostaglandins $I_2$ by using the novel 7-fluoro-prostaglandins.

BACKGROUND OF TECHNOLOGY

7-Fluoroprostaglandins $I_2$ represented by the following formula (III') and having an alternative name of 7-fluoroprostacyclines (or their non-toxic salts when $R^{10}$ is a hydrogen atom), are known, and disclosed in e.g. Japanese Unexamined Patent Publication No. 99580/1982 (GB No. 2088856), Japanese Unexamined Patent Publication No. 165382/1982 (EP No. 54795) or Japanese Unexamined Patent Publication No. 171988/1982 (GB No. 2094310).

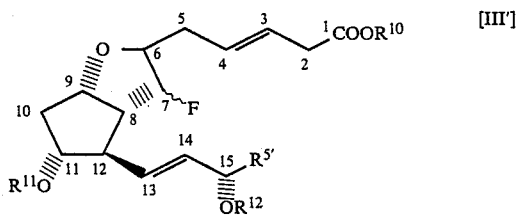

In the formula, $R^{10}$ is a hydrogen atom or an alkyl group having from 1 to 10 carbon atoms, $R^{11}$ and $R^{12}$ are hydrogen atoms or the same or different protective groups, respectively, and $R^{5'}$ is a straight chained or branched alkyl group.

In the above formula (III'), numerals 1 to 15 alloted to the carbon atoms, designate the positions of the carbon atoms.

Natural prostaglandin $I_2$ (hereinafter referred to as "PGI$_2$" including synthesized products) is chemically unstable, and it is difficult to handle it in a neutral or weakly acidic condition. Whereas, 7-fluoroprostaglandins $I_2$ represented by the above formula (III') are extremely stable under the above condition, and believed to be useful from the aspect of the improvement of the selectivity for pharmacological activities. These 7-fluoroprostaglandins $I_2$ are prepared by the fluorination of 7-hydroxy PGI$_2$ (see the above-mentioned Japanese Unexamined Patent Publication No. 165382/1982) or by a process disclosed in the above Japanese Unexamined Patent Publication No. 171988/1982. However, these processes have various problems such as poor yield and selectivity, or the complexity of the reaction steps. Therefore, it has been desired to solve these problems.

SUMMARY OF THE INVENTION

The present invention provides fluorinated novel prostaglandins useful as intermediates for the production of 7-fluoroprostaglandins $I_2$, and a process for their production.

Further, the present invention relates to a process for producing 7-fluoroprostaglandins $I_2$ which are basically known as mentioned above, which is characterized in that the novel 7-fluoroprostaglandins are used as intermediates.

Novel 7-fluoroprostaglandins (hereinafter referred to as 7-FPGF) of the present invention are compounds represented by the following formula (I):

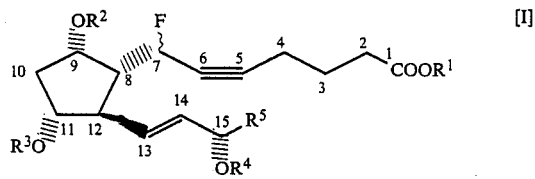

In the formula (I), $R^1$ is a hydrogen atom or an alkyl group having from 1 to 10 carbon atoms, $R^2$, $R^3$ and $R^4$ are hydrogen atoms or the same or different protective groups, respectively, and $R^5$ is a straight chained, branched or cyclic alkyl group having from 3 to 7 carbon atoms.

In the above formula (I), numerals 1 to 15 alloted to the carbon atoms designate the positions of the carbon atoms.

The present invention also relates to a process for producing 7-FPGF represented by the above formula (I) by fluorinating 7-hydroxy- (or trimethylsiloxy-) prostaglandins (hereinafter referred to as 7-XPGF) represented by the following formula (II), optionally followed by the removal of the protective groups and/or hydrolysis.

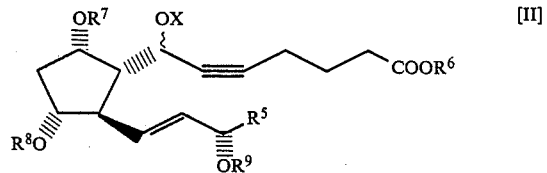

In the formula (II), X is a hydrogen atom or a trimethylsilyl group, $R^6$ is an alkyl group having from 1 to 10 carbon atoms, $R^7$, $R^8$, $R^9$ are the same or different protective groups, respectively, and $R^5$ is the same alkyl group as $R^5$ in the above formula (I).

Furthermore, the present invention relates to a novel process for the production of 7-fluoroprostaglandins $I_2$, wherein 7-fluoroprostaglandins $I_2$ represented by the following formula (III) (or their non-toxic salts when $R^{10}$ is a hydrogen atom) are produced via a cyclization reaction characterized by the use of 7-FPGF represented by the above formula((I).

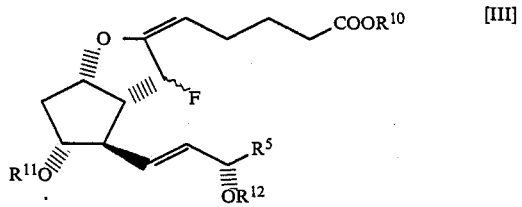

In the formula (III,, $R^{10}$ is a hydrogen atom or an alkyl group having from 1 to 10 carbon atoms, $R^{11}$ and $R^{12}$ are hydrogen atoms or the same or different protective groups, respectively, and $R^5$ is the same alkyl group as $R^5$ in the above formula (I).

The 7-fluoroprostaglandins $I_2$ represented by the formula (III) will be hereinafter referred to as 7-FPGI$_2$.

In the structural formulas such as the above formulas (I) to (III), the tapered line (—) indicates a substituent in a β-orientation (above the plane of the molecule), the dotted line (--) indicates a substituent in an α-orientation (below the plane of the molecule), and a waved line (~) indicates a substituent in an α- or β-orientation or a mixture of these isomers. Further, these compounds include optical isomers, racemic modifications and compounds of other types.

DESCRIPTION FOR CARRYING OUT THE PRESENT INVENTION

In 7-FPGF represented by the above formula (I), $R^1$ is particularly preferably a methyl group or an ethyl group. $R^2$, $R^3$ and $R^4$ are preferably the same or different protective groups. As the protective groups, there may be mentioned a trialkylsilyl group (the three alkyl groups may be the same or different), an alkanoyl group, a tetrahydropyranyl group, a tetrahydrofuranyl group, a benzoyl group, a methoxy ethoxy ethyl group and others. Particularly preferred as the protective group is a trialkylsilyl group having the same or different alkyl groups having from 1 to 4 carbon atoms. As $R^5$, a straight chained alkyl group, particularly a n-amyl group, and a cyclic alkyl group, particularly a cylopentyl group, are particularly preferred. Also in 7-XPGF represented by the formula (II), $R^6$ is the same alkyl group as $R^1$, and $R^7$, $R^8$ and $R^9$ are likewise the same protective groups as $R^2$, $R^3$ and $R^4$. Namely, if $R^6$ to $R^9$ are hydrogen atoms, such portions are likely to be affected by the fluorination reaction. Therefore, as opposed to $R^1$ to $R^4$ in the formula (I), these substituents must not be hydrogen atoms. In the case of 7-FPGI$_2$ represented by the formula (III), $R^{10}$, $R^{11}$ and $R^{12}$ may be the same groups as $R^1$, $R^3$ and $R^4$ in 7-FPGF of the formula (I), or may be different groups, particularly those converted to hydrogen atoms.

In the case where X in 7-XPGF is a trimethylsilyl group, $R^7$, $R^8$ and $R^9$ may be trimethylsilyl groups. However, if they are trimethylsilyl groups, it is possible that the trimethylsilyloxy groups are substituted by fluorine atoms with a fluorinating agent. Particularly, in the case where $R^5$ is a cycloalkyl group, if $R^7$ is a trimethylsilyl group, the yield of 7-FPGF decreases. Therefore, in the case where X is a trimethylsilyl group, $R^7$, $R^8$ and $R^9$ are preferably protective groups other than trimethylsilyl groups. On the other hand, in the case where X in 7-XPGF is a hydrogen atom, even when $R^7$, $R^8$ and $R^9$ are trimethylsilyl groups, the possibility of the substitution of the trimethylsilyloxy groups by the fluorine atoms is minimum since the fluorination reaction conditions are different from those of the former case. However, even when X is a hydrogen atom, $R^7$, $R^8$ and $R^9$ are preferably protective groups other than trimethylsilyl groups in view of the simplicity of the synthesis of 7-XPGF. On the other hand, for the conversion of 7-FPGF to 7-FPGI$_2$, $R^2$ must be a hydrogen atom. Accordingly, in the conversion of 7-XPGF→7-FPGF, $R^7$ =$R^2$ =protective group, whereas in the conversion of 7-FPGF→7-FPGI$_2$, $R^2$ =H. In the conversion of 7-FPGF→7-FPGI$_2$, $R^3$ and $R^4$ may be protective groups or hydrogen atoms. In the former case, $R^8$, $R^3$ and $R^{11}$ may be the same protective groups, and the same applies to $R^9$, $R^4$ and $R^{12}$. In the latter case, at the time when 7-XPGF is synthesized, $R^3$ and $R^4$ are protective groups, and then $R^3$ and $R^4$ will be converted to hydrogen atoms. Taking the entire process from 7-XPGF to 7-FPGI$_2$ into consideration, it is preferred that $R^7$ in 7-XPGF is a protective group different from $R^8$ and $R^{10}$. Because, $R^7$ is required to be converted to a hydrogen atom at an intermediate stage, whereas $R^8$ and $R^9$ are preferably protective groups to the final stage in view of e.g. the yield of the reaction. Accordingly, $R^7$ is preferably a protective group which may more readily be removed than $R^8$ and $R^9$. Particularly preferred is a triethylsilyl group. On the other hand, $R^8$ and $R^9$ are preferably protective groups which are more hardly removable than a trimethylsilyl group and a triethylsilyl group. As $R^8$ or $R^9$, a trialkylsilyl group having at least one alkyl group with at least 3 carbon atoms or a protective group other than the above-mentioned trialkylsilyl groups is preferred. Particularly preferred is a dimethyl-t-butylsilyl group.

In the three types of compounds represented by the formulas (I), (II) and (III), $R^5$ is preferably a n-amyl group or a cyclopentyl group as mentioned above. In the case where $R^5$ is a cycloalkyl group such as a cyclopentyl group, the 7-FPGI$_2$ is novel, and is not disclosed in the above-mentioned prior art references. In the case where $R^5$ is a cycloalkyl group such as a cyclopentyl group, if X is a hydrogen atom, the yield of 7-FPGF in the fluorination of 7-XPGF is extremely low. In the case where $R^5$ is a straight chained or branched (i.e. non-cyclic) alkyl group, if X is a hydrogen atom, the yield of 7-FPGF in the fluorination of 7-XPGF is not so high (i.e. the yield hardly exceeds 50%). Whereas, in the case where X in 7-XPGF is a trimethylsilyl group, the yield of 7-FPGF is high irrespective of the type of $R^5$, i.e. the yield usually exceeds about 60% and can exceed about 70% without difficulty. Thus, it is particularly preferred that X is a trimethylsilyl group. With respect to common organic compounds, it is known that an alcoholic hydroxyl group is fluorinated with a fluorinating agent and thereby substituted by a fluorine atom. However, it has been found for the first time by the present inventors that a trimethylsilyloxy group (i.e. —OSi(CH$_3$)$_3$) can be fluorinated with a fluorinating agent and thus substituted by a fluorine atom. Trialkylsilyloxy groups other than the trimethylsilyloxy group are inactive to the fluorination and can not be substituted by fluorine atoms.

In the cases where $R^5$ is a cycloalkyl group and X is a trimethylsilyl group, the fluorine atom of 7-FPGF obtainable by the fluorination of 7-XPGF has always a β-orientation whether the orientation of the trimethylsilyloxy group in 7-XPGF is an α-orientation or a β-orientation, and it is thereby impossible to obtain 7-FPGF having an α-oriented fluorine atom. On the other hand, in the case where $R^5$ is a non-cyclic alkyl group, the fluorine atom in the resulting 7-FPGF has mainly a β-orientation, but it is believed that a product having an α-orientation is also formed. This stereospecificity in the case of $R^5$ being a cycloalkyl group, is believed to be attributable to the steric hindrance of the cycloalkyl group. The fluorine atom of 7-FPGI$_2$ produced via the cyclization reaction using 7-FPGF having a β-oriented fluorine atom (hereinafter referred to as 7-β-FPGF) has always an α-orientation. Namely, the cyclization reaction peculiarly reverses the orientation of the fluorine atom. The 7-FPGI$_2$ having an α-oriented fluorine atom (hereinafter referred to as 7-α-FPGI$_2$) is believed to be novel. Namely, because 7-FPGI$_2$ disclosed in the above-mentioned prior art references are believed to be 7-β-FPGI$_2$ from the process of their preparation.

Preferred specific compounds as 7-FPGF represented by the formula (I) are the following compounds.

The below mentioned 15-cyclopentyl PGF$_{2\alpha}$ derivatives are PGF$_{2\alpha}$ derivatives having no n-amyl group at 15-position, i.e. 16, 17, 18, 19, 20-pentanor-15-cyclopentyl PGF$_{2\alpha}$ derivatives.

a. 5,6-dehydro-7-fluoro-PGF$_{2\alpha}$.
b. 5,6-dehydro-7-fluoro-PGF$_{2\alpha}$ methyl ester.
c. 5,6-dehydro-7-fluoro-PGF$_{2\alpha}$ ethyl ester.
d. 5,6-dehydro-7-fluoro-PGF$_{2\alpha}$ methyl ester 11,15-bis(-dimethyl-t-butyl)silyl 9-triethylsilyl ether.
e. 5,6-dehydro-7-fluoro-PGF$_{2\alpha}$ methyl ester 11,15-diacetate 9-triethylsilyl ether
f. 5,6-dehydro-7-fluoro- methyl ester 11,15-bis-tetrahydropyranyl ether 9-triethylsilyl ether
g. 5,6-dehydro-7-fluoro-15-cyclopentyl-PGF$_{2\alpha}$.
h. 5,6-dehydro-7-fluoro-15-cyclopentyl-PGF$_{2\alpha}$ methyl ester.
i. 5,6-dehydro-7-fluoro-15-cyclopentyl-PGF$_{2\alpha}$ ethyl ester.
j. 5,6-dehydro-7-fluoro-15-cyclopentyl-PGF$_{2\alpha}$ methyl ester 11,15-bis(dimethyl-t-butyl)silyl 9-triethylsilyl ether.
k. 5,6-dehydro-7-fluoro-15-cyclopentyl-PGF$_{2\alpha}$ methyl ester 11,15-diacetate 9-triethylsilyl ether.
l. 5,6dehydro-7-fluoro-15-cyclopentyl-PGF$_{2\alpha}$ methyl ester 11,15-bis-tetrahydropyranyl ether 9-triethylsilyl ether.

The fluorination of 7-XPGF represented by the formula (II) can be conducted basically in accordance with a conventional method. The fluorination is usually conducted by adding a fluorinating agent to 7-XPGF dissolved in a solvent. As the fluorinating agent, there may be used an amino sulfur trifluoride-type fluorinating agent such as

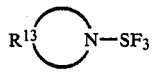

($R^{13}$: a hydrocarbon group forming a ring which has from 4 to 7 carbon atoms and which may contain an oxygen atom) or

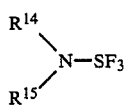

($R^{14}$, $R^{15}$: the same or different alkyl groups having from 1 to 5 carbon atoms), a polyfluoroolefin-dialkylamine-type fluorinating agent (e.g. CF$_3$CHFCF$_2$NEt$_2$, CHClFCF$_2$NEt$_2$), SF$_4$, SeF$_4$, PhSF$_3$, PhPF$_4$, Ph$_3$PF$_2$, etc. Preferred fluorinating agents are amino sulfur trifluoride-type fluorinating agents such as piperidino sulfur trifluoride or diethylaminosulfur trifluoride. In the case where an amino sulfur trifluoride-type fluorinating agent is used as the fluorinating agent, it is preferred to use a base in combination, when X is a hydrogen atom. For instance, pyridine, triethylamine or dimethylaniline may be used. On the other hand, when X is a trimethylsilyl group, the fluorination tends to hardly take place if a base is present. As the solvent, there may be employed a halogenated hydrocarbon such as methylene chloride, dichloromethane, chloroform or carbon tetrachloride, a hydrocarbon such as benzene or toluene, an ether such as tetrahydrofuran or various alkyl ethers, or other solvents. The reaction temperature is usually from $-100°$ to $50°$ C. If necessary, purification may be conducted by means of extraction or chromatography to obtain 7-FPGF i.e. the compounds represented by the formula (I).

The product obtained by the above process, may optionally be subjected to the removal of the protective groups or to hydrolysis. When the protective group is a trialkylsilyl group, the removal of the protective group may suitably be conducted by a method of employing a tetraalkyl ammonium fluoride such as tetrabutyl ammonium fluoride. The tetraalkyl ammonium fluoride may be used in combination with a base such as a trialkylamine. As the solvent, an ether such as tetrahydrofuran is suitable. When the protective group is an acyl group or the like, the removal of the protective group may suitably be conducted by hydrolysis by means of an alkali. Further, in the case where $R^1$ is an alkyl group, it may be converted to a hydrogen atom by a similar alkali hydrolysis. The alkali hydrolysis is preferably conducted by using an aqueous solution of sodium hydroxide, potassium hydroxide or other alkali and optionally in combination with a water soluble organic solvent such as an alcohol. These fluorination, removal of protective groups and hydrolytic reaction are basically known, and are disclosed, for instance, in the above-mentioned Japanese Unexamined Patent Publication No. 165382/1982. The basically known methods may be employed also in the present invention.

The production of 7-FPGI$_2$ represented by the formula (III) may be conducted by using 7-FPGF represented by the above formula (I) and via a cyclization reaction. For this purpose, it is preferred that 7-FPGF represented by the formula (I) is a compound having a hydroxyl group at 9-position unprotected (i.e. $R^2$ is a hydrogen atom) and $R^1$ is an alkyl group. The basic reaction for the cyclization is known and disclosed in "J. Amer. Chem. Soc.", volume 104, from page 5842 to page 5844 (1982). Namely, the cyclization is conducted by means of mercury trifluoroacetate, followed by hydrogenation by means of hydrogenating agent, whereby the desired 7-FPGI$_2$ may be produced. Instead of the trifluoroacetate, mercuric chloride or mercuric acetate may be employed. Further, as the hydrogenating agent, sodium borohydride (NaBH$_4$), zinc borohydride (Zn(BH$_4$)$_2$), etc. may be employed. Depending upon the reaction product, such means as washing, extraction, purification, etc. may optionally be employed to obtain the desired highly pure 7-FPGI$_2$.

7-FPGI$_2$ may be used as it is with $R^{10}$ being an alkyl group, or after converting $R^{10}$ to a hydrogen atom by hydrolysis or by removing the protective group if present, for various purposes as medicines in the same manner as the conventional 7-FPGI$_2$. In the case where $R^{10}$ is a hydrogen atom, 7-FPGI$_2$ may be reacted with various bases to obtain non-toxic salts, which may be employed as medicines. As a such base, an alkali metal hydroxide or (bi)carbonate, an alkaline earth metal hydroxide, ammonia, a mono- or di-alkanolamine, may suitably be used.

The feature of the present invention resides in that by using the above-mentioned preferred fluorinating agent, the fluorination of the carbon atom at the 7-position takes place at an extremely high selectivity, and the yield of 7-FPGF is extremely high. This may be attributable to the fact that the hydroxyl group or trimethylsilyloxy group in 7-XPGF is adjacent to the carbon atom having a triple bond (i.e. the carbon atom at 6-position) and thereby activated. For instance, if the 5- and 6-positions are constituted by a double bond or a single bond, the formation of an olefin or diene due to the dissociation reaction becomes predominant, whereby the yield of 7-FPGF tends to be extremely low. On the other hand, the yield of 7-FPGI by the cyclization reaction of 7-FPGF can be made as high as the yield in the cyclization reaction of the above-mentioned known 5,6-dehydro PGF$_{2\alpha}$. As a whole, the formation of 7-FPGI$_2$ has an extremely high selectivity as compared with the above-mentioned conventional methods.

Further, 7-XPGF represented by the formula (II) is obtainable from the compound represented by the following formula (IV), e.g. a compound of 5,6-dehydro-7-hydroxy-PGF$_{2\alpha}$ alkyl ether with the hydroxyl groups at 11- and 15-positions protected.

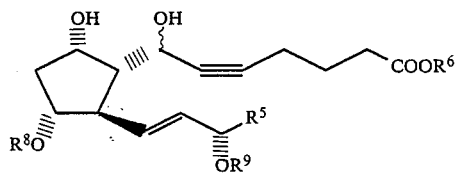

[IV]

In the formula (IV), $R^5$, $R^6$, $R^8$ and $R^9$ are the same as defined in respect of the formula (II).

For instance, firstly a trimethylsilyl group is introduced to the hydroxyl group at 7-position (due to the difference in the reactivity between the two hydroxyl groups, the reaction can be conducted under a condition where the hydroxyl group at 9-position may not be protected by a trimethylsilyl group), and then a triethylsilyl group is introduced to the hydroxyl group at 9-position, whereby 7-XPGF with X being a trimethylsilyl group is obtainable. Further, by removing the protective group of the trimethylsilyl group only from this compound, it is possible to obtain 7-XPGF with X being a hydroxyl group. Further, it is difficult to introduce a protective group to the hydroxyl group at 9-position only of the compound of the formula (IV) in a single step reaction. Further, the compound represented by the above formula (IV) is known, and is disclosed, for instance, in "Tetrahedron Letters" volume 23, pages 5563 to 5566 (1982). Further, 7-XPGF can be synthesized by other methods. For instance, a trimethylsilyl group is introduced to the hydroxyl group at 7-position of the compound represented by the following formula (V), then the oxygen atom bonded to the 9-position is converted to a hydroxyl group, and a triethylsilyl group is introduced to this hydroxyl group, whereby 7-XPGF with X being a trimethylsilyl group is obtainable.

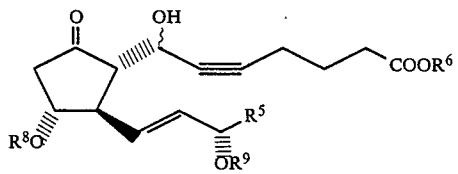

[V]

In the formula (V), $R^5$, $R^6$, $R^8$ and $R^9$ are the same as defined with respect to the formula (II).

Now, the present invention will be described in further detail with reference to Examples. However, the present invention is by no means restricted to these specific Examples.

REFERENCE EXAMPLE

Synthesis of the compound represented by the formula (II)

To an anhydrous acetone solution (8 ml) containing 205 mg (0.336 mmol) of 5,6-dehydro-7-hydroxy-PGF$_{2\alpha}$ methyl ester 11,15-bis(dimethyl-t-butyl)silyl ether (the compound of the formula (IV) wherein $R^5$ is a n-amyl group, $R^6$ is a methyl group, and $R^8$ and $R^9$ are dimethyl-t-butylsilyl groups), 490 $\mu$l(2.59 mmol) of trimethylsilyl diethylamide was dropwise added at $-40°$ C., and the mixture was stirred under the same condition for 2 hours. The mixture was poured into a saturated sodium hydrogen carbonate aqueous solution (20 ml) cooled with ice. The aqueous layer was extracted twice with ethyl ether (10 ml). The organic layer was washed with a saturated sodium chloride aqueous solution, dried over anhydrous magnesium sulfate and then treated under reduced pressure for the removal of low boiling point components, whereby 5,6-dehydro-7-trimethylsiloxy-PGF$_{2\alpha}$ methyl ester 11,15-bis(dimethyl-t-butyl)silyl ether was obtained as a colorless viscous liquid (amount: 230 mg, yield: almost 100%).

The above product was dissolved in anhydrous methylene chloride (2 ml). To this solution, 328 $\mu$l(1.34 mmol) of triethylsilyl diethylamide and then 20 $\mu$l(0.134 mmol) of triethylsilyl chloride were dropwise added at $0°$ C. The mixture was stirred under the same condition for 30 minutes, and then ethyl ether (10 ml) and then a saturated sodium hydrogen carbonate aqueous solution (10 ml) were added. The aqueous layer was extracted twice with ethyl ether (10 ml). The organic layer was washed with a saturated sodium chloride aqueous solution, dried over anhydrous magnesium sulfate and treated under reduced pressure for the removal of low boiling point components, whereby the desired compound 5,6-dehydro-7-trimethylsiloxy-PGF$_{2\alpha}$ methyl ester 11,15-bis(dimethyl-t-butyl)silyl 9-triethylsilyl ether was obtained in a yield of about 95%. This compound will be hereinafter referred to as 7-FPGF-A. $^{13}$C-NMR(CDCl$_3$, TMS, ppm): $\delta$61.5 (C-7), 72.5 (C-11), 73.2 (C-15), 77.2 (C-9).

To the reactor containing 253 mg (0.0319 mmol) of the above product, 3.2 ml of a mixed solution of acetic acid-tetrahydrofuran (hereinafter referred to as THF)-water (8 : 8 : 1) was added at $0°$ C. The mixture was stirred at room temperature for 40 hours, and then low boiling point components were removed under reduced pressure at $0°$ C. To the residue, 10 ml of ethyl ether and 10 ml of a saturated sodium hydrogen carbonate aqueous solution were added, and the aqueous layer was extracted three times with ethyl ether (5 ml). The organic layer was washed with a saturated sodium chloride aqueous solution, dried over anhydrous magnesium sulfate and then concentrated. The product was purified by silica gel column chromatography (hexane/ethyl acetate =70/30), whereby the desired pure compound of 5,6-dehydro-7-hydroxy-PGF$_2$ methyl ester 11,15-bis(dimethyl-t-butyl)silyl 9-triethyl-silyl ether was obtained. This compound will be hereinafter referred to as 7-XPGF-B. The total yield from the starting material (the cmmpound of the formula (IV)) was about 85%.

$^{13}$C-NMR(CDCl$_3$, TMS, ppm):$\delta$63.2 (C-7), 77.0 (C-9), 81.1 (C-5), 84.8 (C-6).

EXAMPLE 1

(Synthesis of the compound represented by the formula (I))

A methylene chloride (1 ml) solution of 134 mg (0.186 mmol) of 7-XPGF-B i.e. the product obtained in the above Reference Example, was dropwise added at −78° C. to a mixture comprising 37 μl(0.372 mmol) of piperidino sulfur trifluoride, 30 μl(0.372 mmol) of pyridine and 1 ml of methylene chloride. Five minutes later, 10 ml of ethyl ether preliminarily cooled to −78° C. was added for dilution, and the mixture was poured into 10 ml of a saturated sodium hydrogen carbonate aqueous solution cooled with ice. The aqueous layer was extracted twice with ether (5 ml), and the ether layer was washed sequentially with 1 N hydrochloric acid cooled with ice, a saturated sodium hydrogen carbonate aqueous solution and a saturated sodium chloride aqueous solution, dried over anhydrous magnesium sulfate and then concentrated under reduced pressure. The residue was purified by column chromatography (hexane/ethyl acetate =95/5), whereby 82 mg (yield: 61%) of 5,6-dehydro-7-fluoro-PGF$_{2\alpha}$ methyl ester 11,15-bis(-dimethyl-t-butyl)silyl 9-triethylsilyl ether (the compound of the formula (I) wherein $R^1$ is a methyl group, $R^2$ is a triethylsilyl group, $R^3$ and $R^4$ are dimethyl-t-butylsilyl groups and $R^5$ is a n-amyl group) was obtained as a colorless liquid.

$^1$H-NMR(CDCl$_3$, TMS, ppm): δ5.17 (1H, td, J=48, 10Hz, C$\underline{H}$F)

$^{13}$C-NMR(CDCl$_3$ TMS, ppm): δ51.4 (C-7 d, J=48 Hz)

EXAMPLE 2

(Compound of the formula (I))

To a THF solution (0.5 ml) containing 72 mg (0.10 mmol) of the fluorinated product obtained in Example 1, 0.5 ml (0.5 mmol) of a 1 mol THF solution of tetrabutyl ammonium fluoride was dropwise added at 0° C., and the mixture was stirred under the same condition for 2 hours. Then, ice water (3 ml) was added, and a 50% sodium chloride aqueous solution (3 ml) was further added. The product was extracted 10 times with 3 ml of ethyl ether/ethyl acetate (1/1). The organic layer was washed with a saturated sodium chloride aqueous solution, dried over anhydrous magnesium sulfate and then concentrated, whereby substantially pure 5,6-dehydro-7-fluoro-PGF$_{2\alpha}$ methyl ester (the compound of the formula (I) wherein $R^1$ is a methyl group, $R^2$, $R^3$ and $R^4$ are hydrogen atoms and $R^5$ is a n-amyl group) was quantitatively obtained.

$^1$H-NMR(CDCl$_3$ TMS, ppm): δ5.20 (1H, td, J=48, 10Hz, C$\underline{H}$F)

EXAMPLE 3

(Preparation of the compound represented by the formula (III))

A THF solution (0.5 ml) containing 47 mg (0.01 mmol) of mercury trifluoroacetate was dropwise added at −78° C. to a THF solution (1 ml) containing 38 mg (0.10 mmol) of the fluorine-containing triol obtained in Example 2. After stirring the mixture under the same conditions for 5 minutes, 28 (0.20 mmol) of triethylamine was dropwise added, and then a mixture comprising 38 mg (1.0 mmol) of sodium borohydride, 4 mg (0.10 mmol) of sodium hydroxide and 1 ml of methanol, was continuously dropwise added under the same condition. The mixture was stirred at −78° C. for 1 hour, then diluted with ethyl ether and filtered through cerite. The filtrate was washed with a saturated sodium chloride aqueous solution, dried over anhydrous magnesium sulfate and then concentrated under reduced pressure. The product was purified by coloumn chromatography (Florisil, hexane/ethyl acetate (1/1) containing 1% of triethylamine), whereby 31 mg of pure 7-fluoro-PGI$_{2\alpha}$ methyl ester (the compound of the formula (III) wherein $R^5$ is a n-amyl group, $R^{10}$ is a methyl group and $R^{11}$ and $R^{12}$ are hydrogen atoms) was obtained (yield: 82%).

$^1$H-NMR(CDCl$_3$, TMS, ppm): δ4.77 (1H, t, J=7Hz, C$\underline{H}$=C[C-5]) 4.93 (1H, bd, J=5Hz, C$\underline{H}$F)

EXAMPLE 4

To a 1,1,2-trichloro-1,2,2-trifluoroethane (hereinafter referred to as R-113) solution (2 ml) containing 140 mg (0.18 mml) of 7-XPGF-A synthesized by the process of the Reference Example, a 1M R-113 solution (0.27 ml, 0.27 mmol) of diethylaminosulfur trifluoride (DAST) was dropwise added at −10° C., and the mixture was stirred at a temperature of from −10° to −5° C. for 17 hours. After diluting it with anhydrous ether, the mixture was poured into a saturated sodium hydrogen carbonate aqueous solution cooled with ice. The ether layer was washed with a saturated sodium chloride aqueous solution, dried over magnesium sulfate and then concentrated under reduced pressure. The residue was purified by Florisil column chromatography (benzene), whereby a pure fluoro product (the compound of the formula (II)) was obtained (60 mg, yield: 53%).

$^1$H-NMR(CDCl$_3$, TMS, ppm : δ5.17 (1H, dm, J=48Hz, C$\underline{H}$F)

EXAMPLE 5

To a methylene chloride solution (8 ml) containing 500 mg (0.82 mmol) of 5,6-dehydro-7-hydroxy-PGF$_{2\alpha}$ methyl ester 11,15-bis(dimethyl-t-butyl)silyl ether, 1.66 ml (20.54 mmol) of pyridine and then 690 μl(4.11 mmol) of trimethylchlorosilane were dropwise added at 0° C., and the mixture was stirred overnight under the same condition. The mixture was poured into a saturated sodium hydrogen carbonate aqueous solution (30 ml) cooled with ice. The aqueous layer was extracted twice with ether. The organic layer was washed with a copper sulfate aqueous solution and a saturated sodium chloride aqueous solution, dried over anhydrous magnesium sulfate and then treated under reduced pressure for the removal of low boiling point components, whereby 5,6-dehydro-7trimethylsiloxy PGF$_{2\alpha}$ a methyl ester 11,15-bis(dimethyl-t-butyl)silyl-9-trimethylsilyl ether was obtained as a colorless viscous liquid (amount: 610 mg, yield: almost 100%).

To an anhydrous R-113 solution (3 ml) containing 159 mg (0.217 mmol) of the above product, 40 μl(0.326 mmol) of diethylamino sulfur trifluoride was dropwise added at -15° C., and the mixture was stirred overnight under the same condition. After diluting it with anhydrous ether, the mixture was poured into a saturated sodium hydrogen carbonate aqueous solution. The ether layer was washed with a saturated sodium chloride aqueous solution, dried over magnesium sulfate and then concentrated under reduced pressure. The product was purified by Florisil column chromatography (benzene), whereby a pure fluoro product was obtained (74 mg, yield: 52%).

$^1$H-NMR: δ5.15 (1H, dm, J=48Hz, C$\underline{H}$F)

EXAMPLE 6

(Preparation of the compound represented by the formula (I))

5,6-Dehydro-7-hydroxy-15-cyclopentyl-PGF$_{2\alpha}$ methyl ester 11,15-bis(dimethyl-t-butyl)silyl 9-triethylsilyl ether (the compound of the formula (II) wherein R$^5$ is a cyclopentyl group, R$^6$ is a methyl group, R$^7$ is a triethylsilyl group and R$^8$ and R$^9$ are dimethyl-t-butylsilyl groups) was synthesized in the same manner as in the Reference Example. By using 140 mg (0.194 mmol) of this compound, 79 mg (yield: 56%) of 5,6-dehydro-7-fluoro-15-cyclopentyl-PGF$_{2\alpha}$ methyl ester 11,15-bis(dimethyl-t-butyl)silyl 9-triethylsilyl ether (the compound of the formula (I) wherein R$^1$ is a methyl group, R$^2$ is a triethylsilyl group, R$^3$ and R$^4$ are dimethyl-t-butylsilyl groups and R$^5$ is a cyclopentyl group) was obtained as a colorless liquid, in the same manner as in Example 1.

$^1$H-NMR(CDCl$_3$, TMS, ppm : δ5.17 (1H, td, J=50, 10Hz, C$\underline{H}$F)

EXAMPLE 7

(The compound represented by the formula (I))

To a THF solution (0.5 ml) containing 61 mg (0.085 mmol) of the compound obtained in Example 6, 1 ml (0.1 mmol) of a 0.1 mol THF solution of tetrabutyl ammonium fluoride and 14μl(0.1 mmol) of triethylamine were added at 0° C. After ascertaining the disappearance of the starting material by thin layer chromatography, volatile products were removed under reduced pressure, and a saturated ammonium sulfate aqueous solution (5 ml) and ethyl acetate (5 ml) were added to the residue. Then, the aqueous layer was extracted twice with ethyl acetate, and the organic layers were put together, dried, concentrated and purified by column chromatography, whereby 5,6-dehydro-7-fluoro-15-cyclopentyl-PGF$_{2\alpha}$ methyl ester 11,15-bis(dimethyl-t-butyl)silyl ether was obtained at a yield of 87%.

EXAMPLE 8

(Preparation of the compound represented by the formula (III))

By using the compound obtained in Example 7, a cyclization reaction was conducted in the same manner as in Example 3, whereby 7-fluoro-15-cyclopentyl PGI$_2$ methyl ester 11,15-bis(dimethyl-t-butyl)silyl ether was obtained. The yield after the purification by column chromatography was 74%.

$^1$H-NMR(CDCl$_3$, TMS, ppm): δ4.76 (1H, t, J=7Hz, C$\underline{H}$=ConC-5)δ4.93 (1H, bd, J=56Hz, C$\underline{H}$F)

EXAMPLE 9

To a methylene chloride solution (8 ml) containing 205 mg (0.336 mmol) of 5,6-dehydro-7-hydroxy-15-cyclopentyl-PGF$_{2\alpha}$ methyl ester 11,15-bis(dimethyl-t-butyl)silyl ether (the compound of the formula (IV) wherein R$^5$ is a cyclopentyl group, R$^6$ is a methyl group, and R$^8$ and R$^9$ are dimethyl-t-butylsilyl groups), 490 μl (2.59 mmol) of trimethylsilyl diethylamide was dropwise added at 0° C., and the mixture was stirred at room temperature for 20 hours. The mixture was poured into a saturated sodium hydrogen carbonate aqueous solution (20 ml) cooled with ice. The aqueous layer was extracted twice with ethyl ether (10 ml). The organic layer was washed with a saturated sodium chloride aqueous solution, dried over anhydrous magnesium sulfate and treated under reduced pressure for the removal of low boiling components, whereby 5,6-dehydro-7,9-bis(trimethyl-siloxy)-15-cyclopentyl-PGF$_{2\alpha}$ methyl ester 11,15-bis(dimethyl-t-butyl)silyl ether (compound of the formula (II)) was obtained as a colorless viscous liquid (amount: 240 mg, yield: 95%).

$^1$H-NMR(CDCl$_3$ TMS, ppm): δ3.60–4.18 (3H, m, —C$\underline{H}$OSi), 4.35–4.60 (1H, m, C≡C-C$\underline{H}$OSi), 5.30–5.50 (2H, m, C$\underline{H}$=C$\underline{H}$)

A R-113 solution of the above product was dropwise added at −30° C. to a mixture of R-113 (2 ml) with piperidino sulfur trifluoride (58 μl, 0.58 mmol). After stirring the mixture at a temperature from −10 to −15° C. for 20 hours, the same treatment as above was conducted, whereby the desired compound (the compound of the formula (I)) was obtained (118 mg, 60%).

$^1$H-NMR(CDCl$_3$, TMS, ppm): δ5.09 (1H, tm, J=50Hz, C$\underline{H}$F)

EXAMPLE 10

To an acetone solution (30 ml) containing 443 mg (0.726 mmol) of 5,6-dehydro-7-hydroxy-15-cyclopentyl-PGF$_{2\alpha}$ methyl ester 11,15-bis(dimethyl-t-butyl)silyl ether, 1.38 ml (7.26 mmol) of trimethylsilyl diethylamide was dropwise added at −20° C., and the mixture was stirred for 20 hours. The reaction solution was diluted with 50 ml of ether, and then poured into 50 ml of a saturated sodium hydrogen carbonate aqueous solution under strong stirring. The aqueous layer was extracted three times wit 50 ml of ether. The organic layer was washed with a saturated sodium chloride aqueous solution and then dried over anhydrous magnesium sulfate. The solvent was removed under reduced pressure, and the residue was purified at 0° C. by silica gel column chromatography (hexane/ethyl acetate =95/5), whereby 464.3 mg (0.655 mmol) [yield: 90.2%] of 5,6-dehydro-7-trimethyl-silyloxy-15-cyclopentyl-PGF$_{2\alpha}$ methyl ester 11,15-bis(dimethyl-t-butyl) silyl ether was obtained.

To a methylene chloride solution (8.4 ml) containing 278 mg (0.408 mmol) of the above product, 1.0 ml (4.09 mmol) of triethylsilyl diethylamide and then 68.3 μl (0.458 mmol) of triethylsilyl chloride were dropwise added at 0° C., and the mixture was stirred at room temperature for 58 hours. The reaction solution was diluted with 20 ml of ether, and then 20 ml of a saturated sodium hydrogen carbonate aqueous solution was added. The aqueous layer was extracted twice with 20 ml of ether. In the same manner as above, washing, drying and the removal of solvent were conducted. The residue was purified at 0° C. by silica gel column chromatography (hexane/ethyl ether =30/1), whereby 317.5 mg (0.400 mmol) [yield: 98.0%] of 5,6-dehydro-7-trimethylsilyloxy-15-cyclopentyl-PGF$_{2\alpha}$ methyl ester 9-triethylsilyl 11,15-bis(dimethyl-t-butyl) silyl ether was obtained.

A R-113 solution (21 ml) containing 461 mg (0.58 ml) of the above product was introduced into a container made of a fluorine resin, and 231 μl(1.74 mmol) of piperidino sulfur trifluoride was dropwise added at 0° C. under an argon atmosphere. The mixture was stirred at room temperature for 8 hours. The reaction solution was diluted with 40 ml of anhydrous ether, and then poured into 60 ml of a saturated sodium hydrogen carbonate aqueous solution under strong stirring by means of a stainless tube under argon pressure. The stirring was continued for 5 minutes. The aqueous layer was extracted three times with 40 ml of ether. The aqueous layer was washed and dried, and the solvent was removed in the same manner as mentioned above. The residue was purified at 0° C. by Florisil column chromatography (hexane/ether =50/1), whereby 260 mg (0.36 mmol) [yield: 62%]of 5,6-dehydro-7-β-fluoro-15-cyclopentyl-PGF$_{2\alpha}$ methyl ester 9-triethylsilyl 11,15-bis(-dimethyl-t-butyl)silyl ether was obtained.

$^{13}$H-NMR(CDCl$_3$, TMS, ppm): δ=83.3 (d, J$_{C.F.}$=165Hz, C-7)

EXAMPLE 11

To an acetonitrile solution (7.2 ml) containing 155 ml (0.214 mmol) of the final product of Example 10, 0.8 ml of triethylamine was added, and 0.8 ml of a 46% hydrogen fluoride aqueous solution was dropwise added at 0° C. The mixture was stirred at room temperature for 20 hours. The reaction solution was diluted with 10 ml of ether, and then poured into a saturated sodium hydrogen carbonate aqueous solution. The mixture was stirred for 5 minutes. The aqueous layer was extracted 10 times with 10 ml of ether, and in the same manner as above, washing, drying and the removal of the solvent were conducted. The residue was purified at 0° C. by Florisil column chromatography (methylene chloride/methanol =50/1) (1% triethylamine)), whereby 69.3 mg (0.181 mmol) [yield: 84.8%] of 5,6-dehydro-7β-fluoro-15-cyclopentyl-PGF$_{2\alpha}$ methyl ester was obtained.

$^1$H-NMR(CDCl$_3$, TMS, ppm): δ6 =3/69 (3H, S, Me), 3.84 (1H, t, J=7.2Hz), 3.97 (1H, bs), 4.46 (1H, bt, J=4.0Hz), 5.30 (1H, dd, J$_{H.F.}$=47.7Hz, J=7.5Hz CHF), 5.53 (1H, dd, J=15.4Hz, J=8.1Hz), 5.62 (1H, dd, J=15.4Hz, J=7.2Hz) $^{13}$C-NMR(CDCl$_3$, TMS, ppm): δ=81.9 (d, J$_{C.F.}$=170Hz, C-7)

EXAMPLE 12

The cyclization of the triol as the final product of Example 11 was conducted. To a tetrahydrofuran solution (11.5 ml) containing 259.5 mg (0.608 mmol) of mercury trifluoroacetate, a tetrahydrofuran solution (11.5 ml) containing 116.2 mg (0.304 ml) of said triol was dropwise added, and the mixture was stirred at −30° C. for 2 hours. Then, 85μl (0.608 mmol) of triethylamine was added at −55° C., and after cooling it to −78° C., a sodium methoxide-1N-methanol solution (3.04 ml) containing 115 mg (3.04 mmol) of sodium borohydride was quickly added, and the mixture was stirred at room temperature for 1 hour. The reaction solution was diluted with 20 ml of ether, and then the solid in the reaction solution was removed by filtration and washed with a saturated sodium chloride aqueous solution. The organic layer was separated, and the aqueous layer was extracted 9 times with 10 ml of ether. In the same manner as above, washing, drying and the removal of the solvent were conducted. The residue was purified by Florisil column chromatography (methylene chloride/acetone =5/1 (1% triethylamine)), whereby 50.6 mg (0.132 mmol) [yield: 43.5%] of 7-α-fluoro-15-cyclo- pentyl-PGI$_2$methyl ester was obtained.

$^{13}$C-NMR(CDCl$_3$, TMS, ppm): δ=91.5 (d, J$_{C.F.}$=188Hz, C-7)

$^1$H-NMR(CDCl$_3$ TMS, ppm): δ5.44 (1H, dd, J$_{H.F.}$=60Hz, J=8.6Hz, CHF)

EXAMPLE 13

5.4 ml (14.1 ml) of the final product obtained in Example 12 was dissolved in 170μl of ethanol. Then, 260μ of a 0.1 N sodium hydroxide aqueous solution was dropwise added at 0° C., and the mixture was stirred at room temperature for 5 hours. The reaction solution was freeze dried, whereby a sodium salt of 7-α-fluoro-15-cyclopentyl-PGI$_2$ was obtained.

We claim:

1. A process for producing a 7-fluoroprostaglandin of formula (I)

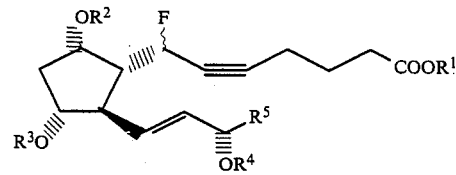

wherein:
$R^1$ is a hydrogen atom or a C$_{1-10}$ alkyl group;
$R^2$, $R^3$ and $R^4$ are each independently a hydrogen atom or a protective group; and
$R^5$ is a linear, branched or cyclic C$_{3-7}$ alkyl group;
said process comprising:
(i) subjecting to the action of an amino sulfur trifluoride compound a prostaglandin of formula (II)

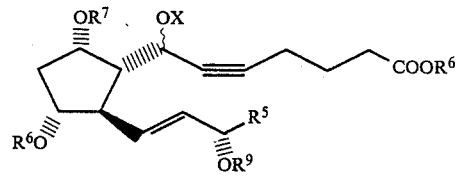

wherein:
X is a trimethylsilyl group;
$R^6$ is a C$_{1-10}$ alkyl group; and $R^7$, $R^8$ and $R^9$ are each independently a protective group; and
(ii) obtaining said 7-fluoroprostaglandin of formula (I).

2. The process of claim 1, comprising using a prostaglandin of formula (II) wherein $R^6$ is a trimethylsilyl group and $R^7$, $R^8$ and $R^9$ are each independently a trialkylsilyl group other than a trimethylsilyl group.

3. The process of claim 1, comprising using a prostaglandin of formula (II) wherein $R^7$ is a triethylsilyl group, and $R^8$ and $R^9$ are each a dimethyl-t-butylsilyl group.

4. The process of claim 1, comprising obtaining a compound of formula (I) having said fluorine atom in an β-orientation.

5. The process of claim 1, comprising using a prostaglandin of formula (II) wherein $R^5$ is a n-amyl group.

6. The process of claim 1, comprising using a prostaglandin of formula (II) wherein $R^5$ is a cyclopentyl group.

7. The process of claim 1, comprising subjecting said compound of formula (I) to hydrolysis to remove said at least one of said protective groups.

8. The process of claim 1, comprising using a prostaglandin of formula (II) wherein said protective group is a trialkylsilyl group, an alkanoyl group, a tetrahydropyranyl group, a tetrahydrofuranyl group, a benzyl group, or a methoxy ethoxy ethyl group.

9. The process of claim 8, comprising using a prostaglandin of formula (II) wherein said trialkylsilyl group is a tri($C_{1-4}$-alkyl)silyl group.

10. The process of claim 1, comprising obtaining
5,6-dehydro-7-fluoro-$PGF_{2\alpha}$;
5,6-dehydro-7-fluoro-$PGF_{2\alpha}$ methyl ester;
5,6-dehydro-7-fluoro-$PGF_{2\alpha}$ ethyl ester;
5,6-dehydro-7-fluoro-$PGF_{2\alpha}$ methyl ester 11,15- bis(-dimethyl-t-butyl)silyl 9-triethylsilyl ether,
5,6-dehydro-7-fluoro-$PGF_{2\alpha}$ methyl ester 11,15diacetate 9-triethylsilyl ether;
5,6-dehydro-7-fluoro-15-cyclopentyl- $PGF_{2\alpha}$;
5,6-dehydro-7-fluoro-15-cyclopentyl-$PGF_{2\alpha}$ methyl ester;
5,6-dehydro-7-fluoro-15-cyclopentyl-$PGF_{2\alpha}$ ehtyl ester;
5,6-dehydro-7-fluoro-15-cyclopentyl-$PGF_{2\alpha}$ methyl ester 11,15-bis(dimethyl-t-butyl)silyl 9-triethylsilyl ester;
5,6-dehydro-7-fluoro-15-cyclopentyl-$PGF_{2\alpha}$ methyl ester 11,15-diacelate 9-triethylsilyl ester; or
5,6-dehydro-7-fluoro-15-cyclopentyl-$PGF_{2\alpha}$ methyl ester 11,15-bis-tetrahydropyranyl ether 9-triethylsilyl ether.

11. The process of claim 1, comprising using as a fluorinating agent an amino sulfur trifluoride-type fluorinating agent of the formula

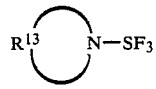

wherein $R^{13}$ is a $C_{4-7}$ hydrocarbon group forming a ring with the nitrogen atom or a $C_{4-7}$ hydrocarbon group interrupted by one oxygen atom and forming a ring with the nitrogen atom, or wherein said amino sulfur trifluoride-type fluorinating agent is $(R^{14})(R^{15})N-SF_3$ wherein $R^{14}$ and $R^{15}$ are each independently a $C_{1-5}$ alkyl group.

12. The process of claim 1, comprising using as said fluorinating agent an amino sulfur trifluoride-type fluorinating agent which is piperidino sulfur trifluoride or diethylaminosulfur trifluoride.

13. The process of claim 1, comprising subjecting said prostaglandin of formula (II) to the action of a fluorinating agent in the presence of a halogenated hydrocarbon solvent, a hydrocarbon solvent or an ether solvent.

14. The process of claim 1, comprising subjecting said prostaglandin of formula (II) to the action of a fluorinating agent at a temperature of from $-100°$ C. to $+50°$ C.

* * * * *